United States Patent
Jager-Lezer et al.

(10) Patent No.: US 6,544,532 B1
(45) Date of Patent: Apr. 8, 2003

(54) COMPOSITION CONTAINING AN UNSTABLE ACTIVE AGENT IN AN OXIDIZING MEDIUM AND USES THEREOF, ESPECIALLY COSMETIC USES

(75) Inventors: Nathalie Jager-Lezer, Bourg la Reine (FR); Raluca Lorant, Thiais (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/701,366

(22) PCT Filed: Mar. 21, 2000

(86) PCT No.: PCT/FR00/00705

§ 371 (c)(1),
(2), (4) Date: Jan. 25, 2001

(87) PCT Pub. No.: WO00/57844

PCT Pub. Date: Oct. 5, 2000

(30) Foreign Application Priority Data

Mar. 31, 1999 (FR) ............................................. 99 04046

(51) Int. Cl.$^7$ .................................................. A61K 7/00
(52) U.S. Cl. ........................ 424/401; 556/444; 556/445; 568/673; 528/31; 528/15; 528/25; 525/474; 525/477; 524/81; 524/261; 524/27; 524/588; 514/553; 514/725; 523/105
(58) Field of Search ................................. 556/444, 445; 568/673; 528/31, 15, 25; 525/474, 477, 81, 261, 27, 588; 514/553, 725; 523/105; 424/401

(56) References Cited

U.S. PATENT DOCUMENTS

| 5,124,313 | A | * | 6/1992 | Schaeffer et al. |
| 5,412,004 | A | * | 5/1995 | Tachibana et al. |
| 6,284,499 | B1 | * | 9/2001 | Kishimoto et al. |
| 6,346,256 | B1 | | 2/2002 | Simon |
| 6,358,500 | B1 | | 3/2002 | Simon |

* cited by examiner

*Primary Examiner*—Robert Dawson
*Assistant Examiner*—Kuo-Liang Peng
(74) *Attorney, Agent, or Firm*—Oblon, Spivak, McClelland, Maier & Neustadt, P.C.

(57) ABSTRACT

The invention relates to a composition containing, in a physiologically acceptable medium, an unstable active agent in an oxidizing medium and an oil phase comprising crosslinked elastomer solid organopolysiloxane particles consisting of at least one oxyalkylene group and oxyethylene in particular. The unstable active agent in an oxidizing medium is stabilized in the inventive composition. The invention also relates to the use of cross-linked elastomer solid organopolysiloxane particles having an oxyalkylene group for the stabilization of an unstable active agent in an oxidizing medium. The unstable active agent can be vitamin C, vitamin A and/or carotenoids. The composition can be anhydrous or take the form of an emulsion. It is particularly suitable for use in cosmetics. It is soft and fresh when applied, spreads easily, is not sticky and does not make the skin or lips dry.

30 Claims, No Drawings

COMPOSITION CONTAINING AN UNSTABLE ACTIVE AGENT IN AN OXIDIZING MEDIUM AND USES THEREOF, ESPECIALLY COSMETIC USES

The invention relates to a composition comprising an active principle, unstable in oxidizing medium, which is stabilized, to the use of the said composition, in particular in the cosmetics field, and to a process for the treatment of human skin using such a composition.

The invention also relates to the use of a crosslinked organopolysiloxane elastomer comprising an oxyalkylene group, for the purpose of stabilizing an active principle which is unstable in oxidizing medium.

It is known to introduce active principles into cosmetic and/or dermatological compositions for the purpose of contributing specific treatments to the skin and/or hair, for example for cleansing the skin, for combating drying, ageing or pigmentation of the skin, for treating acne or certain skin disorders (eczema, psoriasis), for combating excess weight, for promoting restructuring of the skin or its cell replacement, or for treating seborrhoea of the hair.

For example, attempts have been made for a long time to formulate ascorbic acid (or vitamin C) and retinol (vitamin A) in the cosmetic and dermatological fields, in various pharmaceutical dosage forms, because of their numerous beneficial properties. In particular, ascorbic acid stimulates the synthesis of connective tissue and in particular of collagen, reinforces the defences of cutaneous tissue against external attacks, such as ultraviolet radiation and pollution, compensates for vitamin E deficiency in the skin, depigments the skin and has a role in combating free radicals. Due to its properties, ascorbic acid is effective in cleansing the skin and also in combating signs of ageing of the skin, for example in improving the radiance of the complexion and softening fine lines and wrinkles of the skin.

Furthermore, the effects of retinol on cell differentiation make it possible to envisage, inter alia, its use in effectively combating the appearance of wrinkles and fine lines, in effectively combating skin dryness or in effectively combating roughness and/or stiffness of the skin. Repeated application of cosmetic compositions comprising retinol makes it possible, inter alia, to erase wrinkles, to smooth the skin or to repair small tears in the epidermis.

Unfortunately, these active principles are unstable in oxidizing medium and therefore very sensitive to certain environmental parameters, such as, for example, light, oxygen and water. The result of this is therefore a rapid decomposition of these active principles when they are in contact, in particular, with one of these parameters, which runs counter to the desired effectiveness.

In the state of the art, this problem has been dealt with in various ways. Thus, to decrease or slow down the decomposition of ascorbic acid in solution, the document U.S. Pat. No. 5,140,043 recommends stabilizing it by introducing it into aqueous/alcoholic solutions formed of at least 80% water and having a pH of less than 3.5. Due to the high acidity of these solutions, their use in the cosmetics field is difficult to envisage. This is because repeated application of these solutions can disturb the balance of the skin and in particular irritate, indeed even give a burning feeling to, the skin.

Other methods of stabilizing ascorbic acid have been envisaged, in particular by coating (technique disclosed in the document FR-A-1,600,826) or by granulating ascorbic acid (technique illustrated in the document JP-A-53-127819, for the farm produce industry). However, these techniques are, on the one hand, expensive and can, on the other hand, detrimentally affect ascorbic acid, for example during heating, and/or result in compositions which are of little use cosmetically, as is the case with granules.

In addition, the document U.S. Pat. No. 5,853,741 discloses the stabilization of ascorbic acid by non-emulsifying silicone elastomers known under the trade references Gransils from the company Grand Industrie. The disadvantage of these products is that they introduce an oily and greasy effect, without a fresh effect, which does not allow them to be used or only allows them to be used with difficulty in a hot and humid environment and/or by users with greasy skin. Furthermore, these polymers are completely water-repellant and difficult to incorporate in an aqueous phase. Due to their high incompatibility with water and in particular with sweat, the latter is not absorbed by these polymers and even has a tendency to "form beads" at the surface of the skin when the latter perspires.

The stabilization of retinol has also formed the subject of much research. Thus, the document WO-A-93/00085 discloses W/O emulsions comprising retinol and a stabilizing system composed of a chelating agent and an antioxidant. The document EP-A-209,509 has also made known the use of certain polyamino compounds as antioxidants. However, none of the compounds of the prior art makes it possible to obtain satisfactory stabilization of retinol.

The need therefore remains for a composition, which can be used in particular in the cosmetics field, in which an active principle which is unstable in oxidizing medium is stabilized, which is comfortable during application and which does not cause any irritation of the skin after application.

The Applicant Company has now found a composition which overcomes the disadvantages of the prior art.

A subject-matter of the present invention is a composition comprising, in a physiologically acceptable medium, at least one active principle which is unstable in oxidizing medium and an oily phase comprising particles of a crosslinked solid organopolysiloxane elastomer comprising at least one oxyalkylene group, the said composition not being an O/W/O or W/O/W triple emulsion.

By virtue of the presence of the particles of organopolysiloxane elastomer comprising an oxyalkylene group in the composition of the invention, active principles which are unstable in oxidizing medium, such as ascorbic acid and retinol, exhibit better stability and therefore better effectiveness than in a composition not comprising them.

The invention also relates to the use of particles of a crosslinked solid organopolysiloxane elastomer comprising at least one oxyalkylene group for the stabilization of an active principle which is unstable in oxidizing medium.

The term "physiologically acceptable medium" is understood to mean, in the composition of the invention, a non-toxic medium capable of being applied to the skin (including the inside of the eyelids) or the lips of human beings.

The term "solid elastomer" is understood to mean a flexible and deformable material having viscoelastic properties and in particular the consistency of a sponge or of a flexible sphere. Its modulus of elasticity is such that this material is resistant to deformation and has a limited ability to expand and to contract. This material is capable of returning to its original shape after it has been stretched. This elastomer is formed of polymeric chains of high molecular weight, the mobility of which is limited by a uniform network of crosslinking points.

The organopolysiloxanes of the composition of the invention comprise one or more oxyalkylene and in particular oxyethylene (OE) groups, for example from 1 to 40 oxyalkylene units, preferably from 1 to 20 and better still from 10 to 20 oxyalkylene units, which can form polyoxyalkylene and in particular polyoxyethylene chains. These groups can be pendant, at the chain end or intended to connect two parts of the silicone structure. The silicon atoms carrying these groups advantageously number from approximately 1 to 10 and better still from 1 to 6.

Although the invention relates more especially to organopolysiloxanes comprising oxyethylene groups(s) (namely, groups only comprising oxyethylene groups as oxyalkylene groups), it can also relate to organopolysiloxanes comprising oxypropylene group(s), that is to say only comprising oxypropylene groups as oxyalkylene groups. The organopolysiloxanes can also comprise both one or more oxyethylene (OE) group(s), for example 1 to 20, and one or more oxypropylene (OP) group(s), for example 0 to 20; these organopolysiloxanes are also known as organopolysiloxanes comprising alkylethoxy-propylene group(s). The number of oxyethylene groups is preferably greater than the number of oxypropylene groups.

Furthermore, the silicone structure forming the polymeric backbone of the organopolysiloxane comprising oxyalkylene group(s) is advantageously a polydimethylsiloxane (PDMS) structure, a portion of the methyl groups of which is optionally substituted by $C_2$ to $C_{30}$ and preferably $C_8$ to $C_{24}$ and better still from $C_{10}$ to $C_{20}$ alkyl groups or phenyl groups, either at the chain end or at pendant positions.

Furthermore, the organopolysiloxane comprising oxyalkylene group(s) can comprise one or more silicone backbone(s) connected to one another by one or more oxyalkylene and preferably oxyethylene groups as defined above or by one or more alkylene groups, the alkylene group number ranging from 1 to 20 and preferably from 1 to 10. It preferably comprises at least two polymeric backbones connected to one another. The silicone backbone or backbones of the organopolysiloxanes of the composition according to the invention advantageously comprise from 26 to 80 silicon atoms.

The organopolysiloxane elastomers of the composition of the invention exhibit a notable ability to thicken an oily phase and to emulsify an oily phase in an aqueous phase and vice-versa; they swell in the oily phase. They do not dry out the skin and contribute good cosmetic properties, in particular of softness, of freshness and of mattness. These elastomers result in compositions which are comfortable on application, spread well, are soft and are not sticky to the touch. These cosmetic properties are due, on the one hand, to the texture of the organopolysiloxanes and, on the other hand, to their properties, comparable to those of microsponges, of trapping oily media and in particular those of the composition and those secreted by the skin.

The organopolysiloxane elastomers used in the composition in accordance with the invention are partially or completely crosslinked and have a three-dimensional structure. When included in an oily phase, they are converted, according to the level of oily phase used, from a product with a spongy appearance, when they are used in the presence of small contents of oily phase, to a homogeneous gel, in the presence of larger amounts of oily phase. The gelling of the oily phase by these elastomers can be complete or partial.

The elastomers of the invention are provided in the form of a powder or gel comprising an organopolysiloxane elastomer with a three-dimensional structure dispersed in an oily phase. This oily phase, also known as liquid fatty phase, can comprise any non-aqueous substance or mixture of non-aqueous substances which is liquid at room temperature (25° C.) and at atmospheric pressure (760 mm of Hg).

The organopolysiloxane elastomers used according to the invention can be chosen from the crosslinked polymers obtained by an addition and crosslinking reaction in a non-aqueous medium, in the presence of a catalyst, in particular of the platinum type, of at least:

(a) one first organopolysiloxane (i) having at least two vinyl groups in the αω-position of the silicone chain; and
(b) one second organopolysiloxane (ii) having at least one hydrogen atom bonded to a silicon atom per molecule and at least one oxyalkylene, in particular oxyethylene, group.

The organopolysiloxane (i) is chosen in particular from polydimethylsiloxanes (PDMSs) and is more especially an α,ω-dimethylvinylpolydimethylsiloxane. The organopolysiloxane (ii) is chosen in particular from polydimethylsiloxanes comprising one or more hydrogen atom(s), each bonded to a silicon atom, and one or more oxyethylene groups and optionally one or more oxypropylene groups bonded to a silicon atom via an alkylene radical having from 1 to 22 carbon atoms.

The silicone chains of the first and second organopolysiloxanes (i) and (ii) optionally comprise $C_1$ to $C_6$ alkyl pendant chains and/or aryl chains.

The organopolysiloxane elastomers of the composition according to the invention are advantageously provided in any oily phase with which it constitutes an anhydrous gel. This gel can in particular be obtained as follows:

(a) mixing the first organopolysiloxane (i) and the second organopolysiloxane (ii);
(b) adding the oily phase to the mixture of stage (a); and
(c) polymerizing the first organopolysiloxane (i) and the second organopolysiloxane (ii) in the oily phase in the presence of a platinum catalyst.

The oily phase used during the manufacture of the anhydrous gel comprises one or more oils which are liquid are room temperature (25° C.) chosen from hydrocarbonaceous oils (ie. which only comprise carbons and hydrogens) and/or silicone oils. The oily phase is advantageously a silicone liquid phase comprising one or more oils chosen from polydimethylsiloxanes (PDMS) with a linear or cyclic chain which are liquid at room temperature, optionally comprising a pendant alkyl or aryl chain or an alkyl or aryl chain at the chain end, the alkyl chain having from 1 to 6 carbon atoms.

The organopolysiloxanes of the invention are obtained in particular according to the procedure of Examples 3, 4 and 8 of the document U.S. Pat. No. 5,412,004 and of the examples of the document U.S. Pat. No. 5,811,487.

The organopolysiloxanes of the composition of the invention are, for example, that sold under the reference KSG 21 by the company Shin Etsu or the product of Example 3 (synthetic example) of U.S. Pat. No. 5,412,004.

KSG 21 is in the form of a pasty gel comprising about 28% polyorganosiloxane and 72% silicone oil (PDMS) having a viscosity of 6 cSt (i.e. $6 \times 10^{-6}$ m$^2$/s).

According to a preferred embodiment of the invention, use is made of a product of Example 3 (synthesis example) of Patent U.S. Pat. No. 5,412,004. This product is provided in the form of a pasty gel comprising approximately 33% by weight of crosslinked organopolysiloxane comprising oxyethylene group(s) and approximately 67% of 6 cSt PDMS (i.e. $6 \times 10^{-6}$ m$^2$/s). The organopolysiloxane comprises approximately 18% by weight of ethylene oxide with respect to the total weight of the polymer.

The elastomer gel used in the composition of the invention has a plastic Theological behaviour exhibiting a viscosity, at low shear in the region of $10^{-3}s^{-1}$ or $10^{-4}s^{-1}$, ranging from $2 \times 10^6$ poises to $4 \times 10^6$ poises ($2 \times 10^5$ Pa·s to $4 \times 10^5$ Pa·s) and a dynamic viscosity of from 15 to 50 poises (1.5 to 5 Pa·s) for a shear rate of $200 \text{ s}^{-1}$ at $t_{10}$ minutes, measured with an RS 75 (Haake) controlled-stress rheometer at 25° C. in cone/plate geometry; characteristics of the cone: diameter of 20 mm, angle of 1° and gap of 40 μm. This organopolysiloxane additionally has a viscoelastic behaviour with a dominant elastic nature at low values of the shear stress defined as follows: 800 Pa<$G^*_{plateau}$<2500 Pa with $\delta_{plateau}$ in the region of 10°, $G^*_{plateau}$ representing the stiffness modulus (or complex modulus), ie. the consistency and being measured at 1 Hz, and $\delta_{plateau}$ representing the elasticity or loss angle. It exhibits a flash point of approximately 170° C. at atmospheric pressure.

For the product of Example 3 (synthesis example) of document U.S. Pat. No. 5,412,004, the dynamic viscosity, under the conditions given above, is 45 Poises (4.5 Pa·s).

The organopolysiloxane elastomer gel used in the composition of the invention is preferably present in the composition in a content ranging from 0.5 to 99% by weight and better still from 3 to 75% by weight with respect to the total weight of the composition, which corresponds to a level of organopolysiloxane elastomer, as active material, of 0.1 to 33% by weight and better still of 1 to 25% by weight with respect to the total weight of the composition.

In particular, the particles of organopolysiloxane elastomer (as active material) have a size ranging from 0.1 to 500 μm, preferably from 3 to 200 μm and better still from 3 to 500 μm. These particles can be spherical, flat or amorphous with preferably a spherical shape.

The organopolysiloxane elastomer of the invention is in particular a surfactant with an HLB (Hydrophilic-Lipophilic Balance) of approximately 2.5. It is therefore suited to the manufacture of water-in-oil emulsions. It can also make possible, in combination with another appropriate surfactant, the preparation of oil-in-water emulsions.

This organopolysiloxane elastomer gel can be used in combination with an additional oily phase which can comprise fatty substances which are liquid at room temperature, waxes or gums which are solid at room temperature, or pasty fatty substances of animal, vegetable, mineral or synthetic origin and their mixtures.

The additional oily phase can have any nature and can comprise products which are liquid at room temperature, such as silicone, fluorinated, fluorosilicone or optionally partially silicone-comprising hydrocarbonaceous oils. These oils can be volatile at room temperature and at atmospheric pressure. The term "volatile oil" is understood to mean in particular an oil capable of evaporating, in less than one hour, on contact with the skin or lips which has in particular a non-zero vapour pressure, especially ranging from $10^{-3}$ to 300 mm of Hg (at room temperature and atmospheric pressure) and preferably greater than 0.3 mm of Hg.

The amount of fatty substance in the composition according to the invention can range from 1 to 80% by weight, preferably from 1 to 50% and better still from 1 to 30% by weight with respect to the total weight of the composition.

Mention may in particular be made, as oils which can be used in the composition of the invention, of:

hydrocarbonaceous oils of animal origin, such as perhydrosqualene;

hydrocarbonaceous oils of vegetable origin, such as liquid fatty acid triglycerides, for example sunflower, maize, soybean, gourd, grape seed, sesame, hazelnut, apricot, macadamia, castor or avocado oils, or triglycerides of caprylic/capric acids, such as those sold by the company Stéarineries Dubois or those sold under the names Miglyol 810, 812 and 818 by the company Dynamit Nobel;

oils of formula $R^1COOR^2$, in which $R^1$ represents the residue of a higher fatty acid comprising from 7 to 19 carbon atoms and $R^2$ represents a branched hydrocarbonaceous chain comprising from 3 to 20 carbon atoms, such as, for example, purcellin oil, isopropyl myristate, or octanoates, decanoates or ricinoleates of alcohols or of polyalcohols;

linear or branched hydrocarbons of mineral or synthetic origin, such as volatile or non-volatile liquid paraffins and their derivatives, liquid petrolatum, polydecenes or hydrogenated polyisobutene, such as parleam;

synthetic ethers of formula $R^3OR^4$, in which $R^3$ is a $C_3$ to $C_{19}$ alkyl radical and $R^4$ a $C_3$ to $C_{20}$ alkyl radical;

fatty alcohols, such as octyldodecanol or oleyl alcohol;

fluorinated oils which are partially hydrocarbonaceous and/or silicone-comprising, such as perfluoropolyesters;

silicone oils, such as polymethylsiloxanes with a linear or cyclic silicone chain which are liquid or pasty at room temperature, phenyl dimethicones, phenyl trimethicones, polymethylphenylsiloxanes, and alkylpolydimethylsiloxanes with a $C_2$ to $C_{20}$ alkyl chain;

their mixtures.

The gel formed of organopolysiloxane comprising oxyethylene group(s) makes it possible to structure these oils in the form of a novel texture of "custard tart" type which is devoid of oily gelling agent which would interfere with the soft/silky and pleasant feel of the composition.

The composition of the invention makes it possible to stabilize any active principle which is unstable in oxidizing medium and mention may in particular be made, as active principles which are unstable in oxidizing medium, of vitamins and in particular ascorbic acid (vitamin C) and its derivatives, in particular its glycosylated and phosphated derivatives and its esters, such as ascorbyl acetate, palmitate and propionate, retinol (vitamin A) and its derivatives, in particular its esters, such as retinol acetate, palmitate and propionate; urea; rutin; enzymes, such as lipase, protease, phospholipase and cellulases; natural extracts, such as green tea, balm extract, thyme extract, or procyanidol oligomers (PCO), such as hawthorn PCO, pine PCO and grape PCO; certain acids, such as kojic acid, caffeic acid, retinoic acid and its derivatives, or 1,4-di(3-methylidene-10-camphorsulphonic acid); carotenoids, such as carotenes, like, for example, α-, β- and γ-carotenes, β,φ-carotene, ξ-carotene, β,γ-carotene or lycopene (ψ,ψ-carotene); polyunsaturated fatty acids, such as γ-linolenic acid, and their mixtures.

It can also relate to any natural or synthetic compound which can comprise the active principles indicated above, in particular plant extracts and more especially fruit extracts.

The composition of the invention is particularly advantageous in stabilizing vitamins, in particular vitamin C and vitamin A, and carotenoids, in particular lycopene.

The amount of active principle which is unstable in oxidizing medium in the composition according to the invention depends on the type of active principle used and on the desired goal. The active principle or principles can generally be used in the composition according to the invention in an amount ranging from 0.01 to 20% by weight, preferably from 0.04 to 15% and better still from 0.1 to 10% by weight with respect to the total weight of the composition.

According to the hydrophilic or lipophilic nature of the active principles used, the latter are introduced into the oily phase of the composition or into an aqueous phase added to the composition. The latter can therefore be provided in the form of an anhydrous product or in the form of an oil-inwater or water-in-oil emulsion or of a multiple emulsion other than a W/O/W or O/W/O emulsion. The term "emulsion" is understood to mean here both emulsifier-free dispersions and dispersions comprising emulsifiers or alternatively dispersions stabilized by solid particles or by lipid spherules of ionic or non-ionic type. Thus, retinol, which is lipophilic, can be introduced into a completely anhydrous composition whereas ascorbic acid, which is hydrophilic, is preferably introduced into the aqueous phase of an emulsion.

Furthermore, the composition of the invention can be more or less fluid and can have the appearance of a lotion, of a gel, of a cream or of a cast product and can even be provided in the form of an aerosol.

When the composition according to the invention is anhydrous, the oily phase, including the amount of the organopolysiloxane elastomer or elastomers, is present in a concentration ranging from 80 to 99.95% and preferably from 90 to 99.9% of the total weight of the composition.

In the compositions of the invention in the form of emulsion, the aqueous phase of the composition is present in a concentration ranging from 1 to 75%, preferably 20 to 70% and better still from 40 to 70% of the total weight of the composition and the oily phase, including the amount of the organopolysiloxane elastomer or elastomers, is present in a concentration ranging from 25 to 99%, preferably from 30 to 80% and better still from 30 to 60% of the total weight of the composition.

Advantageously, when the composition of the invention is a W/O emulsion, it is devoid of surfactant other than the organopolysiloxane elastomer used according to the invention. Advantageously, when the composition of the invention is a W/O emulsion, it is free of surfactant other than the elastomeric polyorganosiloxane used according to the invention. However, it can optionally contain a surfactant, preferably a silicone surfactant such as, for example, the dimethicone copolyol/cyclomethicone (10/90) mixtures sold under the names "DC-3225 C" and "DC-5225C" by the company Dow Corning.

When it is in the form of an O/W emulsion, the composition of the invention preferably comprises at least one other emulsifier. Mention may be made, as emulsifier for O/W emulsions, of, for example, the oxyethylenated polydimethylsiloxane (dimethicone copolyol) sold under the name "DC2-5695" by the company Dow Corning.

The emulsifier or emulsifiers can be present in the composition according to the invention in a concentration which can vary to a large extent. Thus, this concentration can range, for example, from 0.1 to 20% and preferably from 1 to 5% by weight with respect to the total weight of the composition.

In order to further increase the stability of the active principles which are unstable in oxidizing medium, the composition of the invention can also advantageously comprise at least one compound chosen from metal-sequestering agents, metabisulphites and polyols.

The metal-sequestering agent can be in particular be a phosphonic acid derivative. Mention may in particular be made, as phosphonic acid derivatives which can be used in the composition of the invention, of ethylenediaminetetra (methylenephosphonic acid), hexamethylenediaminetetra (methylenephosphonic acid), diethylenetriaminepenta (methylenephosphonic acid) and their salts and in particular their sodium salts, such as the pentasodium salt of ethylenediaminetetra(methylenephosphonic acid). Use is advantageously made of ethylenediaminetetra (methylenephosphonic acid), sold in particular by the Company Monsanto under the name Dequest 2041, and the pentasodium salt of this acid sold under the name Dequest 2046 by the Company Monsanto.

When it is present, the sequestering agent is in a concentration generally ranging from 0.05 to 0.5% by weight with respect to the total weight of the composition.

The metabisulphite can be an alkali metal, alkaline earth metal or ammonium salt of anhydro-sulphurous acid. Use is preferably made of sodium or potassium bisulphite. When it is present, the metabisulphite is in a concentration generally ranging from 0.005 to 5% and preferably from 0.05 to 1% by weight with respect to the total weight of the composition.

The polyols optionally present in the composition of the invention can, for example, be chosen from glycerol, glycols, such as propyleneglycol and polyethyleneglycol, and silicones comprising hydroxyl groups. The polyols are present in a concentration preferably ranging from 0.5 to 30% and preferably from 5 to 25% of the total weight of the composition.

The composition of the invention can be used in particular in topical application, in particular in the cosmetic and dermatological fields. This composition can be more or less fluid and have the appearance of a white or coloured cream, of an ointment, of a milk, of a lotion, of a serum, of a paste or of a foam. The composition of the invention can be applied topically to the face, including around the eyes, to the body and to the scalp of human beings.

In a known way, the composition of the invention can also comprise additives usual in the cosmetic and dermatological fields, such as hydrophilic or lipophilic active principles other than active principles which are unstable in oxidizing medium, preservatives, antioxidants, solvents, fillers, odour absorbers and colouring materials, in so far as the additive does not destabilize the active principle present in the composition. The amounts of these various additives are those conventionally used in the fields under consideration, for example from 0.01 to 20% of the total weight of the composition. These additives, according to their nature, can be introduced into the oily phase or into the aqueous phase.

Mention may in particular be made, as hydrophilic gelling agents, of carboxyvinyl polymers (carbomer), acrylic copolymers, such as acrylate/alkyl acrylate copolymers, polyacrylamides, polysaccharides, natural gums and clays and mention may be made, as lipophilic gelling agents, of modified clays, such as bentones, metal salts of fatty acids, hydrophobic silica and polyethylenes. Use may in particular be made, as gelling agents, of the product sold under the name of Sepigel 305 by the company Seppic (CTFA name: polyacrylamide/C13-14 isoparaffin/Laureth-7) and the product sold under the name of Hostacerin AMPS by the company Hoechst (CTFA name: ammonium polyacryldimethyltauramide).

The composition of the invention can be used in all the applications of the unstable active principles described above and in particular for cleansing the skin and/or for treating it, in particular for toning it up, regenerating it, for treating wrinkles and/or fine lines of the skin, for improving the complexion, for removing pigmentary blemishes of the skin, for combating damage due to UV radiation and/or for strengthening cutaneous tissues against attacks from the environment.

Another subject-matter of the present invention is consequently the cosmetic use of the composition according to the invention for cleansing the skin and/or for treating the skin and in particular for toning it up, regenerating it, for treating wrinkles and/or fine lines of the skin, for improving the complexion, for removing pigmentary blemishes of the skin, for combating damage due to UV radiation and/or for strengthening cutaneous tissues against attacks from the environment.

A final subject-matter of the invention is a cosmetic process for cleansing and/or treating the skin which consists in applying, to the skin, including around the eyes, a composition in accordance with the invention.

Another subject-matter of the invention is the use of the composition according to the invention in the manufacture of a cream intended for a treatment of the skin.

Other advantages and characteristics of the invention will become more fully apparent on reading the examples, given by way of illustration and without implied limitation. The amounts are given therein as % by weight, except when otherwise mentioned.

Example 1

Cream for the Face (W/O Emulsion)

| Oily phase: | |
|---|---|
| Cyclomethicone | 10% |
| Phenyl trimethicone (Dow Corning 556 Fluid) | 4% |
| Apricot oil | 3% |
| Modified silicone (Example 3 of U.S. Pat. No. -5,412,004) | 20% |

(i.e. 6.6% of active material)

| Aqueous phase: | |
|---|---|
| Glycerol | 23% |
| Propylene glycol | 6% |
| Sodium hydroxide | 1.8% |
| Citric acid | 1.2% |
| Ascorbic acid | 5% |
| Deionized water | q.s. 100% |

The emulsion is prepared by preparing the phases and introducing the aqueous phase into the oily phase with stirring under cold conditions.

The composition obtained is provided in the form of a cream appropriate for caring for the face which is soft on application. This cream gives immediate radiance to the complexion and makes it possible to smooth out the imperfections.

The stability of the ascorbic acid in the emulsion has been observed to be good and the stability of the emulsion itself has been observed to be good.

Example 2

Cream for the Face (W/O Emulsion)

| Oily phase: | |
|---|---|
| Dimethicone copolyol/cyclomethicone (10/90) (DC-5225C) | 20% |
| Phenyl trimethicone (Dow Corning 556 Fluid) | 4% |
| Apricot oil | 3% |
| Nylon-12 | 5% |

| -continued | |
|---|---|
| Oily phase: | |
| Modified silicone (KSG 21 comprising 28% of active material) | 5% |

(i.e. 1.4% of active material)

| Aqueous phase: | |
|---|---|
| Glycerol | 23% |
| Disodium EDTA | 0.05% |
| Propylene glycol | 4% |
| Sodium hydroxide | 1.8% |
| Citric acid | 1.2% |
| Ascorbic acid | 5% |
| Deionized water | q.s. 100% |

Procedure: The oily phase is prepared, the constituents of the aqueous phase are mixed, the nylon being added last, and then emulsification is carried out by pouring the aqueous phase into the oily phase with stirring.

The composition obtained is provided in the form of a cream appropriate for caring for the face which is soft on application. This cream gives immediate radiance to the complexion and makes it possible to smooth out the imperfections.

The stability of the ascorbic acid in the emulsion has been observed to be good and the stability of the emulsion itself has been observed to be good, even after centrifuging.

Comparative Example

The same emulsion as that of Example 2 but not comprising KSG-21 separates into two phases and destabilizes after centrifuging.

Example 3

Cream for the Face (W/O Emulsion)

| Oily phase: | |
|---|---|
| Dimethicone copolyol/cyclomethicone (10/90) (DC-5225C) | 20% |
| Phenyl trimethicone (Dow Corning 556 Fluid) | 4% |
| Apricot oil | 3% |
| Octyl isononanoate | 1.2% |
| Nylon-12 | 5% |
| Modified silicone (KSG 21 comprising 28% of active material) | 3.75% |

(i.e. 1.4% of active material)

| Aqueous phase: | |
|---|---|
| Glycerol | 23% |
| Disodium EDTA | 0.05% |
| Propylene glycol | 4% |
| Sodium hydroxide | 1.8% |
| Citric acid | 1.2% |
| Ascorbic acid | 5% |
| Deionized water | q.s. 100% |

The emulsion is prepared according to the same process as in Example 2.

The emulsion obtained is stable and is capable of making the complexion radiant and of smoothing out skin imperfections.

What is claimed is:

1. A composition comprising, in a physiologically acceptable medium, at least one active principle which is unstable in oxidizing medium and an oily phase comprising an active principle stabilizing amount of particles of a crosslinked solid organopolysiloxane elastomer comprising at least one oxyalkylene group, wherein said composition is not an O/W/O or W/O/W triple emulsion.

2. The composition according to claim 1, wherein the organopolysiloxane elastomer comprises at least one oxyethylene group.

3. The composition according to claim 1, wherein the organopolysiloxane elastomer only comprises oxyethylene groups as oxyalkylene groups.

4. The composition according to claim 1, wherein the organopolysiloxane elastomer is obtained by an addition and crosslinking reaction in a non-aqueous medium, in the presence of a catalyst, of at least:
one first organopolysiloxane (i) having at least two vinyl groups in the α,ω-position of the silicone chain per molecule; and
one second organopolysiloxane (ii) having at least one hydrogen atom bonded to a silicon atom per molecule and at least one oxyalkylene group.

5. The composition according to claim 4, wherein the first organopolysiloxane (i) is chosen from polydimethylsiloxanes.

6. The composition according to claim 4, wherein the first organopolysiloxane (i) is an α,ω-dimethylvinylpolydimethylsiloxane.

7. The composition according to claim 4, wherein the second organopolysiloxane (ii) is chosen from polydimethylsiloxanes comprising one or more hydrogen atoms and one or more oxyalkylene groups bonded to a silicon atom via an alkylene radical having from 1 to 22 carbon atoms.

8. The composition according to claim 4, wherein the organopolysiloxane particles are in the form of a gel obtained according to the following stages:
(a) mixing the first and second organopolysiloxanes (i) and (ii);
(b) adding the oily phase to the mixture of stage (a);
(c) polymerizing the first and second organopolysiloxanes (i) and (ii) in the oily phase in the presence of a platinum catalyst.

9. The composition according to claim 8, wherein the gel has a stiffness modulus $G^*_{plateau}$ measured at 1 Hz which is defined as follows: 800 Pa$<G^*_{plateau}<$2500 Pa with $\delta_{plateau}$ in the region of 10°, $\delta_{plateau}$ representing the elasticity.

10. The composition according to claim 1, wherein the elastomeric organosiloxane particles have a size ranging from 3 to 200 μm.

11. The composition according to claim 1, wherein the organopolysiloxane elastomer represents from 0.1 to 33% of active material by weight with respect to the total weight of the composition.

12. The composition according to claim 1, wherein the oily phase comprises one or more liquid hydrocarbonaceous and/or silicone oils.

13. The composition according to claim 1, further comprising at least one fatty substance chosen from volatile and non-volatile oils or from waxes, gums and pasty fatty substances of animal, vegetable, mineral or synthetic origin, and their mixtures.

14. The composition according to claim 13, wherein the amount of fatty substance ranges from 1 to 80% by weight with respect to the total weight of the composition.

15. The composition according to claim 1, further comprising an aqueous phase representing from 1 to 75% of the total weight of the composition.

16. The composition according to claim 1, wherein the active principle which is unstable in oxidizing medium is selected from the group consisting of vitamins, urea, rutin, enzymes, carotenoids, natural extracts, polyunsaturated fatty acids and their mixtures.

17. The composition according to claim 1, wherein the active principle which is unstable in oxidizing medium is chosen from vitamin C, vitamin A, carotenes and their mixtures.

18. The composition according to claim 1, further comprising at least one compound selected from the group consisting of metal-sequestering agents, metabisulphites and polyols.

19. The composition according to claim 1, which comprises an anhydrous product or an emulsion.

20. A method for cleansing the skin and/or for treating the skin and in particular for toning it up, regenerating it, for treating wrinkles and/or fine lines of the skin, for improving the complexion, for removing pigmentary blemishes of the skin, for combating damage due to UV radiation and/or for strengthening cutaneous tissues against attacks from the environment comprising applying the composition according to claim 1 to the skin.

21. A cosmetic process for cleansing and/or treating the skin which comprises applying to the skin a composition according to claim 1.

22. A method for treating wrinkles and/or fine lines comprising applying to the skin a composition according to claim 1.

23. A method for stabilizing an active principle which is unstable in oxidizing medium comprising combining the active principle with a stabilizing amount of a crosslinked solid organopolysiloxane elastomer comprising at least one oxyalkylene group.

24. The method according to claim 22, wherein the particles of organopolysiloxane elastomer are obtained by an addition and crosslinking reaction in a non-aqueous medium, in the presence of a catalyst, of at least:
one first organopolysiloxane (i) having at least two vinyl groups in the α,ω-position of the silicone chain per molecule; and
one second organopolysiloxane (ii) having at least one hydrogen atom bonded to a silicon atom per molecule and at least one oxyalkylene group.

25. The composition according to claim 1, further comprising an aqueous phase representing from 20 to 70% of the total weight of the composition.

26. The composition of according to claim 1, wherein the active principle is selected from the group consisting of ascorbic acid, ascorbyl acetate, ascorbyl palmitate and ascorbyl propionate.

27. The composition of according to claim 1, wherein the active principle is selected from the group consisting of retinol, retinyl acetate, retinyl palmitate, and retinyl propionate.

28. The composition of according to claim 1, wherein the active principle is selected from the group consisting of kojic acid, caffeic acid and retinoic acid.

29. The composition of according to claim 1, wherein the active principle is selected from the group consisting of retinol and retinyl palmitate.

30. The composition of according to claim 1, wherein the active principle is ascorbic acid.

* * * * *